(12) United States Patent
Leshchiner et al.

US009149534B2

(10) Patent No.: US 9,149,534 B2
(45) Date of Patent: *Oct. 6, 2015

(54) COMPOSITION USING CROSS-LINKED HYALURONIC ACID FOR TOPICAL COSMETIC AND THERAPEUTIC APPLICATIONS

(71) Applicant: LuroMed LLC, Orangeburg, NY (US)

(72) Inventors: Adelya K. Leshchiner, Cresskill, NJ (US); Nancy E. Larsen, Highland Mills, NY (US); Edward G. Parent, North Bergen, NJ (US)

(73) Assignee: Luromed LLC, Orangeburg, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/604,054

(22) Filed: Jan. 23, 2015

(65) Prior Publication Data

US 2015/0132237 A1 May 14, 2015

Related U.S. Application Data

(63) Continuation of application No. 14/217,869, filed on Mar. 18, 2014, now Pat. No. 8,940,281, and a continuation of application No. 12/315,087, filed on Nov. 28, 2008, now Pat. No. 8,679,470.

(51) Int. Cl.
| | | |
|---|---|---|
| *A61Q 17/04* | (2006.01) | |
| *A61K 47/36* | (2006.01) | |
| *A61K 8/60* | (2006.01) | |
| *A61K 8/36* | (2006.01) | |
| *A61K 8/73* | (2006.01) | |
| *A61K 38/12* | (2006.01) | |
| *A61K 31/573* | (2006.01) | |
| *A61K 31/79* | (2006.01) | |
| *A61K 8/67* | (2006.01) | |
| *A61K 8/37* | (2006.01) | |
| *A61K 31/165* | (2006.01) | |
| *A61K 8/04* | (2006.01) | |
| *A61K 9/00* | (2006.01) | |
| *A61K 31/00* | (2006.01) | |
| *A61K 31/4015* | (2006.01) | |
| *A61K 33/18* | (2006.01) | |
| *A61K 45/06* | (2006.01) | |
| *A61Q 19/00* | (2006.01) | |

(52) U.S. Cl.
CPC .................. *A61K 47/36* (2013.01); *A61K 8/042* (2013.01); *A61K 8/36* (2013.01); *A61K 8/37* (2013.01); *A61K 8/60* (2013.01); *A61K 8/676* (2013.01); *A61K 8/735* (2013.01); *A61K 9/0014* (2013.01); *A61K 9/0046* (2013.01); *A61K 31/00* (2013.01); *A61K 31/165* (2013.01); *A61K 31/4015* (2013.01); *A61K 31/573* (2013.01); *A61K 31/79* (2013.01); *A61K 33/18* (2013.01); *A61K 38/12* (2013.01); *A61K 45/06* (2013.01); *A61Q 17/04* (2013.01); *A61Q 19/00* (2013.01)

(58) Field of Classification Search
CPC ........... A61K 47/36; A61K 8/37; A61K 8/60; A61K 8/36; A61K 8/735; A61K 38/12; A61K 31/573; A61K 31/79; A61K 8/676; A61K 31/165; A61Q 17/04
See application file for complete search history.

(56) References Cited

U.S. PATENT DOCUMENTS

| | | | |
|---|---|---|---|
| 4,582,865 | A | 4/1986 | Balazs et al. |
| 4,605,691 | A | 8/1986 | Balazs et al. |
| 4,636,524 | A | 1/1987 | Balazs et al. |
| 5,143,724 | A | 9/1992 | Leshchiner et al. |
| 5,246,698 | A | 9/1993 | Leshchiner et al. |
| 5,399,351 | A | 3/1995 | Leshchiner et al. |
| 5,633,001 | A | 5/1997 | Bengt |
| 5,911,980 | A | 6/1999 | Samour et al. |
| 6,218,373 | B1 | 4/2001 | Falk et al. |
| 6,235,312 | B1 | 5/2001 | Hobbs et al. |
| 6,316,011 | B1 | 11/2001 | Ron et al. |
| 6,495,149 | B1 | 12/2002 | Scavone et al. |
| 6,509,322 | B2 | 1/2003 | Benedetti et al. |
| 6,719,740 | B2 | 4/2004 | Burnett et al. |
| 6,746,689 | B2 | 6/2004 | Fischer et al. |
| 6,824,785 | B1 | 11/2004 | Kitson et al. |
| 7,521,434 | B2 | 4/2009 | Leshchiner et al. |
| 7,858,000 | B2 | 12/2010 | Winterton |
| 8,679,470 | B2 | 3/2014 | Leshchiner et al. |
| 8,940,281 | B2 | 1/2015 | Leshchiner et al. |
| 2003/0099712 | A1 | 5/2003 | Jayaraman |

(Continued)

FOREIGN PATENT DOCUMENTS

EP 0224987 A2 6/1987

OTHER PUBLICATIONS

Mensitieri et al. "The rheological behavior of animal vitreus and its comparison with vitreal substitutes", Journal of Material Science: Materials in Medicine (1994), 743-747.

(Continued)

*Primary Examiner* — Johann R Richter
*Assistant Examiner* — Genevieve S Alley
(74) *Attorney, Agent, or Firm* — Nutter McClennen & Fish LLP; Konstantin Linnik

(57) ABSTRACT

Disclosed are compositions comprising crosslinked hyaluronic acid gels, preferably vinyl sulfone cross-linked hyaluronic acid known as hylan B gel, for use in topical cosmetic and dermatological formulations. The hylan B gel in these formulations provides prolonged delivery of incorporated substances to the surface of the skin, to provide a hydrated film on the surface of the skin, and to provide a substantive and compatible film on the skin.

12 Claims, 1 Drawing Sheet

(56) References Cited

U.S. PATENT DOCUMENTS

| | | |
|---|---|---|
| 2004/0091604 A1 | 5/2004 | Dempsey et al. |
| 2004/0109832 A1 | 6/2004 | Harichian et al. |
| 2006/0088604 A1 | 4/2006 | Sisterman |
| 2006/0280809 A1 | 12/2006 | Leshchiner et al. |
| 2006/0293277 A1 | 12/2006 | Leshchiner et al. |
| 2007/0036745 A1 | 2/2007 | Leshchiner et al. |
| 2010/0276638 A1 | 11/2010 | Liu et al. |

OTHER PUBLICATIONS

Schwarz et al. "A Bound Form of Silicon in Glycosaminoglcans and Polyuronides", Proceedings of the National Academy of Sciences of the United States of America, (May 1973) vol. 70, No. 5, pp. 1608-1612.

Tomihata et al. "Preparation of cross-linked hyaluronic acid films of low water content" Biomaterials, 1997, vol. 18, pp. 189-195.

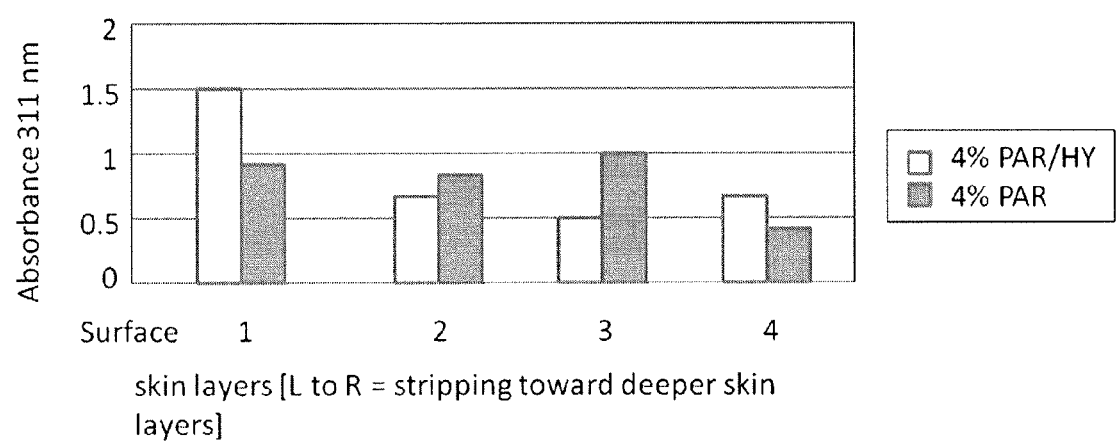

COMPOSITION USING CROSS-LINKED HYALURONIC ACID FOR TOPICAL COSMETIC AND THERAPEUTIC APPLICATIONS

BACKGROUND OF THE INVENTION

1. Field of the Invention

The present invention relates to compositions containing cross-linked hyaluronic acid (HA) gels including, but not limited to, hylan B gel, for use in topical cosmetic and dermatological applications.

2. Description of Related Art

Topical skin care product compositions often contain a variety of natural and/or synthetic polymeric substances, for the purpose of delivering active ingredients to the surface of the skin and/or providing moisturization of the skin. For example, U.S. Pat. No. 5,911,980 describes the use of lipophilic and amphiphilic or hydrophilic film-forming polymer compositions as a topical agent for the delivery of agents to the skin.

U.S. Pat. No. 6,824,785 discloses multi-compartment or multi-layered structures that may be loaded with an active ingredient for dermal delivery. Lipids, typically in the form of liposomes are used to provide an epidermal barrier when applied topically to the skin, which reduces trans-epidermal water loss.

U.S. Pat. No. 6,719,740 describes a delivery system, comprised of a top layer and a bottom layer attached to each other, with a pouch that contains the skin care ingredient between the two layers.

U.S. Pat. No. 6,746,689 describes method for administering an active ingredient where a local anesthetic is combined with an intradermal penetration agent.

U.S. Pat. No. 6,316,011 describes a reverse thermally viscosifying composition including a linear block copolymer, wherein at least one block comprises a polyoxamer having a hydrophobic region and a hydrophilic region effective to form micelles in response to a change in temperature, and at least one block comprises a bioadhesive polymer or oligomer in an aqueous medium for the administration of a pharmaceutical agent to the skin.

U.S. Pat. No. 6,495,149 describes the use of a liquid carrier for delivery of an active comprised of cyclomethicone liquid for topical, leave-on compositions.

U.S. Pat. No. 6,235,312 describes the use of liquid crystalline phase drug delivery systems for topical delivery to the skin, wherein the liquid crystalline phase is comprised of a mono glyceride.

Several patents disclose compositions containing cross-linked hyaluronic acid gels for use in topical formulations. For example, U.S. Pat. No. 4,582,865 describes cross-linked gels of hyaluronic acid or mixed cross-linked gels of hyaluronic acid, wherein the gels further comprise at least one other hydrophilic polymer having a functional group capable of reacting with divinyl sulfone and either an inert water insoluble substance or a low molecular weight substance covalently bonded to the macromolecular network, and methods of making these gels.

U.S. Pat. No. 4,605,691 describes methods of preparing a cross-linked gel of hyaluronic acid comprising subjecting sodium hyaluronate in a dilute aqueous alkaline solution at a pH of not less than about 9 to a cross-linking reaction with divinyl sulfone at about 20° C. and a cross-linked gel of hyaluronic acid produced by this method.

U.S. Pat. No. 4,636,524 describes a delivery system for a substance having biological or pharmacological activity comprising a molecular cage formed of a cross-linked gel of hyaluronic acid or a mixed cross-linked gel of hyaluronic acid and at least one other hydrophilic polymer and containing a diffusible substance having biological or pharmacological activity.

U.S. Pat. No. 5,143,724 describes biocompatible gel slurries consisting of two phases: a particulate gel phase comprised of a chemically cross-linked polymeric gel and a second, fluid phase comprising a polymer solution of a water-soluble biocompatible polymer in the aqueous medium, wherein the fluid phase has a pH in the range of 5.0-8.0.

U.S. Pat. No. 5,246,698 describes methods of making the slurries of U.S. Pat. No. 5,143,724.

U.S. Pat. No. 5,399,351 describes methods of using these slurries to control adhesion formation between tissues of a living body resulting from surgical intervention.

European Patent 0224987 describes drug delivery systems based on hyaluronic acid and its salts and derivatives thereof in soluble or non-soluble cross-linked forms, which serve as a vehicle for slow release of a drug from a system.

BRIEF SUMMARY OF THE INVENTION

The present invention, in one aspect thereof, provides compositions comprising cross-linked hyaluronic acid (HA) gels including, but not limited to, hylan B gel, for use in topical cosmetic and dermatological applications. The hylan B gel acts as a hydrated molecular cage as that term is described in U.S. Pat. No. 4,636,524, and into which one may incorporate and entrap substances, including water, for delivery thereof to the surface of the skin. Typically, the composition contains an active ingredient at a concentration of 0-100%, preferably 0.1-50% and most preferably, 10-20% by weight of the total composition.

In another aspect thereof, the invention provides a topical composition comprising (a) a polysaccharide gel matrix, in combination with (b) another substance, which may be (i) a hydrophilic organic ingredient, such as an α-, β-, γ- or δ-hydroxy acid, an α-amino acid, a β-amino acid, a γ-amino acid, a δ-amino acid, a glycerin, a vitamin or their derivatives, a sugar, an essential oil, a water-soluble oil, a fragrance, a natural polymer, a synthetic polymer, a cross-linked natural polymer, a cross-linked synthetic polymer, a peptide, a protein, a polysaccharide or a nucleic acid; wherein the concentration of the hydrophilic organic ingredient may be from 0-100%, preferably, 0.1-10% and most preferably, from 1-5% by weight based on the entire composition (ii) a hydrophobic organic ingredient, such as a petrolatum, a fatty acid, a fatty alcohol, an oil, a lipid or a silicone; wherein the concentration of the hydrophobic organic ingredient may be from 0-100%, preferably 0.1-50% by weight based on the weight of the entire composition; (iii) an inorganic ingredient such as titanium dioxide, silica, calcium chloride, kaolin, talc or tantalum, alone, wherein the concentration of the inorganic ingredient may be from 0-100%, preferably 0.1-4% by weight based on the weight of the entire composition, said inorganic ingredient being present alone, or in combination with, an effective amount of a therapeutic agent deliverable to a skin surface, wherein the therapeutic agent is a salt, a solvate, a prodrug, and a derivative of the therapeutic agent, and wherein the substance, alone or in combination, is entrapped within the matrix. In this embodiment, the therapeutic agent is an anti-inflammatory agent such as a steroid, for example, hydrocortisone, hydrocortisone acetate or prednison, an antiseptic agent, such as iodine, an anti-infective agent, i.e., an antibiotic such as bacitracin, a mucous membrane agent, a cleansing agent, a preservative, an astringent, an antihistamine, an analgesic, an anesthetic, an acne medication, an antifungal agent, an anti-pruritic agent, a hormone, a growth factor, a moisturizing agent, a sunscreen such as Parsol MCX, a hyperpigmentation agent, an antioxidant or a nutritional agent which is a vitamin or a mineral. The amount of the therapeutic agent present in the composition may be anywhere from 0% up to the specific recommended dosage for each such specific therapeutic agent. For example, in the case of an antibiotic such as bacitracin, the specific dosage will typically be about 500 units per gram of the composition in the form of an ointment. In the case of a steroid, such as hydrocortisone, the specified dosage will typically be about 0.25-1% by weight, and in the case of a therapeutic agent such as capsaicin, the specified dosage will typically be in the amount of about 0.25% by weight of the entire composition.

In another embodiment, the therapeutic agent of the composition is a mixture of the anti-inflammatory agent and the anti-infective agent.

In another embodiment, the invention provides a composition wherein the polysaccharide of the composition is a cross-linked polymer of hyaluronic acid, a salt of the polymer or a derivative of the polymer.

In yet another embodiment of the invention, the polymer is in an equilibrium or non-equilibrium form and is hylan B, where the hylan B concentration is from about 0.4-20% by weight.

BRIEF DESCRIPTION OF THE FIGURE

FIG. 1 illustrates higher levels of sunscreen on the surface of skin in the presence of HY. 0.1 gm samples of each sunscreen composition were weighed out onto weigh paper squares, and then each applied to designated, marked areas on the washed forearm of human volunteers. After 2 hours each area was swabbed with a cotton tip applicator, then the site was stripped 8 times using Cuderm® stripping disks. Each disk was placed into a test tube containing 3 ml of isopropanol, 2 disks were placed per tube, to elute the Parsol sunscreen from the skin on the disk. The absorbance of the isopropanol in each tube was measured at λ max 311 nm). The data in the graph indicate that higher levels of sunscreen are present on the uppermost layers of the skin, and that there is more sunscreen on the surface of the skin in the sample containing Hylasome (far left side of graph). Deeper layers of the skin contain less sunscreen, but show a trend toward more sunscreen being absorbed into the skin from the control (non-Hylasome) samples. Surface Retention of sunscreen at 2 hours is shown for four surfaces.

DETAILED DESCRIPTION OF THE INVENTION

The compositions of the present invention, which contain crosslinked hyaluronic acid (HA) gels including, but not limited to, hylan B gel, are compositions for use in topical cosmetic and dermatological applications and in which hylan B gel is used as a hydrated molecular cage into which one may incorporate, entrap and deliver substances, including water, to the surface of the skin. The hylan B gel may be either in equilibrium or non-equilibrium form. In the non-equilibrium form, the gel is not fully swollen, while in the equilibrium form, the gel is swollen fully and cannot swell further. Hylan B gel matrix is derived from hyaluronic acid, otherwise known as hyaluronan or HA, and is a vinyl sulfone cross-linked derivative of hyaluronic acid. The hylan B gel matrix has an unusually high capacity to bind water, and in particular, to a greater degree than other natural and synthetic polymers [Takigami et al., *Carbohydrate Polymers* 26N: 11-18 (1995)]. Water, which is a slightly bound portion of the gel matrix and which forms reservoirs in which ingredients can be incorporated or trapped, is effectively delivered to the skin because of its bound state.

The ingredients which are incorporated into, or entrapped, within the hylan B gel matrix (equilibrated or non-equilibrated) include, but are not limited to, some classes of organic compounds, inorganic compounds, and mixtures thereof.

Among the organic compounds included are hydrophilic organic substances including, but not limited to an α-, β-, γ- or δ-hydroxy acid, α-, β-, γ-, and δ-amino acids, glycerin, vitamins and their derivatives, sugars, essential oils, water soluble oils and fragrances, low molecular weight and high molecular weight substances including natural and synthetic polymers, cross-linked natural and synthetic polymers, peptides, proteins, water soluble hydrophilic proteins, such as albumins, polysaccharides, nucleic acids, and mixtures thereof. The organic compounds also include, but are not limited to, hydrophobic organic substances, including, but not limited to, petrolatum, fatty acids, fatty alcohols, oils, lipids, silicones, and mixtures thereof. Among the inorganic compounds and substances included are substances such as, but not limited to, titanium dioxide, silica, calcium chloride, kaolin, talc, tantalum and mixtures thereof.

Ingredients included in these chemical categories include active ingredients, drugs, prodrugs and nondrugs. They include, but are not limited to, the pharmaceutical categories of anti-inflammatory agents, antiseptics, anti-infectives, mucous membrane agents, cleansing agents, preservatives, astringents, antihistamines, analgesics, capsaicin, acne medications, antifungals, antipruritics, hormones, growth factors, moisturizers, sunscreens, hyperpigmentation agents, antioxidants, nutritional substances, including, but not limited to, vitamins and minerals, substances of botanical, marine and animal origin, homeopathic substances and mixtures thereof. As should be clear from the foregoing description, very many different types of materials can be and are capable of being incorporated into the hylan B gel for the purpose of delivering them to the skin of a host, typically, a human, but not necessarily a human.

An advantage of this invention is the ability to provide prolonged and effective delivery of incorporated ingredients to the surface of the skin and, where applicable to provide increased protection from the irritant effects of some active ingredients, for example, from the burning sensations produced by some active ingredients, e.g., capsaicin. Additionally, one can provide a hydrated film on the surface of the skin in which certain ingredients have been incorporated, and which contains water in the form of slightly bound water, and as well, to provide a substantive and compatible film on the surface of the skin.

Hyaluronan or hyaluronic acid (HA) is a naturally occurring polysaccharide that consists of alternating N-acetyl-D-glucosamine and D-glucuronic acid monosaccharide units linked with alternating [beta] 1-3 glucoronidic (?) and [beta] 1-4 glucosaminidic (?) bonds. The molecular weight of hyaluronic acid is generally within the range of $5 \times 10^4$ up to more than $8 \times 10^6$ Daltons. Cross-linked HA gels include, but are not limited to, hylan B gel matrix, which is a vinyl sulfone cross-linked derivative of hyaluronic acid. Cross linked simple and mixed gels based on hyaluronan, products containing such gels, and methods to prepare same are described in U.S. Pat. Nos. 4,582,865, 4,605,691 and 4,636,524, which are noted above in the Description of Related Art, and the contents of which are incorporated by reference herein. It should also be clearly understood that hyaluronan of any origin may be successfully used for the purposes of this invention.

The compositions or-the present invention may be administered in dosage unit formulations containing conventional nontoxic pharmaceutically acceptable carriers, adjuvants, and vehicles as desired. Topical administration also may involve the use of transdermal administration such as transdermal patches or iontophoresis devices which are prepared according to techniques and procedures well known in the art.

The amount of the compositions of the present invention which will be effective in the treatment of a particular disorder or condition will depend on the nature of the disorder or condition, and can be determined by standard clinical techniques. See, for example, Goodman and Gilman; The Physician's Desk Reference, Medical Economics Company, Inc., Oradell, N.J., 1995; and Drug Facts and Comparisons, Facts and, Comparisons, Inc., St. Louis, Mo., 1993. The precise dose to be employed in any particular formulation will also depend on the seriousness of the disease or disorder, and should be decided upon and determined according to the judgment of the practitioner and each patient's specific circumstances.

Unless defined otherwise, all technical and scientific terms used herein have the same meaning as is commonly understood by one of ordinary skill in the art to which this invention pertains. Although any methods and materials similar or equivalent to those described herein can also be used in the practice or testing of the present invention, the preferred methods and materials will now be described. All publications mentioned herein, are incorporated herein by reference to disclose and describe the methods and/or materials in connection with which the publications are cited. Unless indicated otherwise, parts are parts by weight, molecular weight is weight average molecular weight, temperature is in degrees Centigrade, and pressure is at or near atmospheric.

The term "effective amount" is used herein to denote that amount of an agent that will elicit the response of a mammal, including a human, that is being sought for the purpose of effecting a desired therapeutic effect. The term "therapeutically effective amount" is used herein to denote that amount of a drug or pharmaceutical agent or a pharmaceutically acceptable salt, solvate or prodrug thereof, that will elicit the therapeutic response of an animal or human that is being sought.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention has been described with reference to the preferred embodiments to illustrate the principles of the invention and not to limit the invention to the particular embodiments illustrated. Modifications and alterations may occur to others upon reading and understanding the preceding detailed description. It is intended that the scope of the invention be construed as including all modifications and alterations that may occur to others upon reading and understanding the preceding detailed description insofar as they come within the scope of the following claims or equivalents thereof.

The invention is described in more detail and with respect to only some, but not all embodiments thereof in the following examples, which are not intended to limit the scope of the claims.

As will be evident from the following examples, the properties of the topical compositions of the present invention are superior to those described in the prior art mentioned above. The present compositions all form a permeable, hydrated film on the surface of the skin, require no environmental stimulus, such as temperature change, to deliver, since delivery of the active occurs upon application of the compositions to the skin, and they suffer from little or no temperature sensitivity, and therefore experience no marked changes in the physical state of the composition upon exposure to high and low ambient temperatures.

Example 1

This example illustrates the preparation of nonequilibrium gel of hyaluronic acid (Hylasome a sodium hyaluronate cross-polymer) with a polymer concentration of approximately 1%. 30 gm of sodium hyaluronate (HA) of bacterial origin were dissolved in 853 gm of distilled water. To this solution 100 gm of 1N NaOH were added to achieve a final concentration of 0.1N alkali. The mixture was stirred carefully until uniform. To this solution a mixture of 7 gm (6 ml) of divinyl sulfone (DVS) in 10 gm of water was added and stirred until a strong gel was formed with an HA concentration of approximately 3%; typically 15-20 minutes for completion of the cross-linking reaction. The resultant gel (approximately 1 kg) was placed into dialysis tubing (32 mm diameter, 12000-14000 molecular weight cut-off, Spectrum) so that the gel occupied approximately one-third of the length of the dialysis tubing. The end of the dialysis tubing was sealed and the gel manually distributed throughout the length of the tubing in order to facilitate uniform swelling. The sealed tubing containing gel was placed into a clean container with five liters of purified water; the water was changed twice daily until the pH of the gel inside the tubing was neutral (pH 6-7). The neutral, washed gel was expelled from the dialysis tubing. The gel was carefully mixed with a preservative (15 gm of phenonip dispersed in about 100 gm of water, to a final phenonip concentration of 0.5%) until uniform. The concentration of HA in the nonequilibrium gel was approximately 1% (10 mg/ml). The designation "%" refers to the concentration of HA in the gel, calculated based on the amount of dry HA polymer present in the gel.

Example 2

Hylasome (HA 0.1%)

This example illustrates the preparation of a swollen HA gel with a polymer concentration of 0.1%. To prepare 1 kg of this gel Hylasome (HA 1%) in an amount of 100 gm was used. The Hylasome (HA 1%) was prepared according to Example 1. To 896 gm of RO (reverse osmosis) water were added 4 gm of phenonip preservative and the mixture was stirred until a uniform fine dispersion formed and then added to 100 gm of Hylasome (HA 1%). The resultant swollen gel was then disintegrated using a high shear mixer (Silverson) using a low shear mixer blade, at a speed of 4000 rpm, for 4 minutes per 1 kg volume. The homogenized gel had a swelling ratio of 1,000. This material was used in some cosmetic and dermatological formulations as a highly effective hydrating component which slowly delivers water. Hylasome (HA 0.1%) is a partially equilibrated gel and can be further swollen with additional water and/or other active ingredients.

Example 3

Hylasome (HA 0.05%)

This example illustrates the preparation of 1 kg of fully swollen equilibrated gel with an HA concentration of 0.05%. This equilibrated gel can be made either from Hylasome (HA 1%) by adding 50 gm of this gel to 896 gm of RO water and 4 gm of phenonip preservative or by adding 500 gm of Hylasome (HA 0.1%) to 500 gm of RO water and 2.23 gm of phenonip. The subsequent procedures are the same as described in Example 2. Hylasome (HA 1%) was prepared according to Example 1, and Hylasome (HA 0.1%) was prepared according to Example 2. The resultant Hylasorne (HA 0.05%) has a swelling ratio of 2,000.

Example 4

This example illustrates the preparation of a formulation containing Hylasome swollen with a solution of the sugars, glucose and mannitol.

Step 1: Preparation of the Active Ingredient—Hylasome Swollen with a Solution of Glucose and Mannitol.

To prepare 100 gm of this composition, to 62.6 gm of water was added 0.4 gm of phenonip and mixed until a uniform dispersion formed. To this mixture were added 10.0 gm of D-mannitol and 13.5 gm of glucose. This mixture was stirred until the sugars dissolved. Upon dissolution 13.5 gm of Hylasome (HA 1%) were added and the mixture stirred until the slurry was uniform. The Hylasome gel slurry was then homogenized according to the procedure described in Example 1. The concentration of sugars in the gel was 23.5%. The polymer concentration was 0.135%.

| Parts | | Ingredients | % (g/100 gm) |
|---|---|---|---|
| 1A | 1 | Carbopol 940 | 0.36 |
| | 2 | water | 53.67 |
| | 3 | EDTA | 0.14 |
| | 4 | Germaben II | 0.75 |
| 1B | 1 | Cucumber extract | 0.24 |
| | 2 | Aloe vera gel | 0.16 |
| | 3 | Chamomile extract | 0.24 |
| | 4 | Glucam E-20 | 3.15 |
| | 5 | Apricot extract | 0.24 |
| | 6 | Carrot extract | 0.24 |
| | 7 | Tea extract | 1.3 |
| | 8 | Eye bright extract | 0.24 |
| | 9 | TEA (triethanolamine) | 0.7 |
| 1C | 1 | Cellosize Polymer PCG019, 2% with 5% alcohol | 4.72 1.58 |
| | 2 | HA 1% | 0.24 |
| | 3 | Polyox Coag 1% | 0.48 |
| | 4 | Hydrosoy 2000 | |

| Parts | | Ingredients | % (g/100 gm) |
|---|---|---|---|
| 1D | | Rose Natural, water soluble | 0.16 |
| 1E | | Dye - Orange/Red 2:1, 0.1% | 0.12 |
| Part 2 | 1 | Mannitol | 2.97 |
| Hylasome | 2 | Gluose | 4.00 |
| sugars | 3 | water | 18.58 |
| | 4 | Hylasome | 4.00 |
| | 5 | Phenonip | 0.12 |
| | | TOTAL | 29.67 |
| Part 3 | 1 | HA 1% | 0.32 |
| | 2 | Hydrosoy 2000 | 0.16 |
| | 3 | DxS | 0.004 |
| | 4 | Water | 1.09 |
| | 5 | TEA (triethanolamine) | 0.0006 |
| | 6 | phenonip | 0.16 |
| | | TOTAL | 1.73 |

Step 2: Preparation of a Dermatological Formulation Containing Hylasome Swollen with a Solution of 23.5% Sugars.

This formulation was prepared as follows: Carbopol was dispersed in water and the mixture was stirred until a uniform dispersion formed. The preservatives EDTA and Germaben II were then added. The ingredients in Parts B and C were blended. Parts A and B were heated to 45-50° C. while mixing separately, then combined together, stirred well and cooled to 40° C.

The components of Part C were blended and then heated to 40° C. and added to the combined Parts A and B, mixed carefully until uniform and then cooled to room temperature (20-25° C.). Part D was added and mixed, and then Part E was added and mixed by careful stirring. This mixture constitutes Part 1. To Part 1 was added the Hylasome/sugars slurry and after mixing, Part 3 was added. Part 3 was prepared by blending the listed ingredients. The pH of the composition was neutral (6-7). The sugar content was approximately 7%. This dermatological composition is used as a remedy for puffiness and minor swelling.

Example 5

Preparation of a face mask using Hylasome swollen with 47% lactic acid as active ingredient (INCI [International Nomenclature Cosmetic Ingredient] name sodium hyaluronate cross-polymer and lactic acid).

Step 1: Preparation of Hylasome Swollen with 47% Lactic Acid.

All ingredients in the following table except Hylasome were mixed. When mixing was complete, Hylasome was added and mixed until swollen. The mixture was homogenized until it became liquidy and uniform.

| INGREDIENT | %, gm/100 gm |
|---|---|
| D-manoitol | 2 |
| Tris-amino | 10 |
| Glycerol | 2.6 |
| Lactic acid | 47 |
| Phenonip | 0.4 |
| RO water | 18 |
| Hylasome (HA 1%) | 20 |

Step 2: Preparation of the Basic Formulation, Containing the Active Ingredient Hylasome Swollen with Lactic Acid.

This formulation was prepared in several stages, as follows: Part A1 was prepared by dissolving pluronics (?) in water; Part A2 was made by dispersing Carbopol 940 in water and then adding the preservatives EDTA and Germaben II. Then Parts A1 and A2 were combined. The ingredients in Part B and C were blended; Parts A1, A2, and B were then heated to 70-75° C. while mixing separately, then they were combined and mixing was continued at 70-75° C. until uniform, followed by cooling to 45° C. Parts C and F were mixed, then combined and heated to 45° C., and added to Parts A1+A2+B. This blend was cooled to room temperature, ca. 25° C. The pH of this mixture was neutral (6-7) adjusted by TEA (Part D). To this basic formulation was added the active ingredient Hylasome swollen with 47% lactic acid (Part E). The pH of the formulation was approximately 3.5.

| Part | Ingredients | % (g/100 g) |
|---|---|---|
| A$_1$ | 1 Water | 35.57 |
| | 2 Pluronic 87 | 1.90 |
| | 3 Pluronic 127 | 0.95 |
| A$_2$ | 1 Water | 36.02 |
| | 2 EDTA | 0.14 |
| | 3 Germaben II | 0.50 |
| | 4 Carbopol | 0.48 |
| B | 1 TEA (triethanolamine) | 0.19 |
| | 2 Tween 20 | 0.95 |
| | 3 Polydimethylsiloxane (fluid 200) | 0.95 |
| | 4 Phosal 50 PG | 0.90 |
| | 5 Beeswax | 0.95 |
| | 6 Robane (squalene) | 1.43 |
| | 7 Lanoxide -59 | 0.95 |
| | 8 Coconut oil | 0.48 |
| | 9 Cetyl alcohol | 1.90 |
| | 10 Propylene glycol | 1.90 |
| | 11 Glycerol monostearate | 0.95 |
| | 12 Glucam E-20 | 1.90 |
| | 13 Germaben II | 0.50 |
| | 14 Chamomile extract | 0.19 |
| | 15 Lemon Bioflavonoids extract | 0.48 |
| | 16 *Calendula* extract | 0.19 |
| | 17 Apricot fruit extract | 0.10 |
| | 18 Peppermint extract | 0.05 |
| C | 1 HA 1% | 0.95 |
| | 2 Cellosize 2% (polymer PCG-10) | 1.45 |
| | 3 Jasmine/Rosewood Natural, water soluble | 0.24 |
| | 4 Lavender Natural, water soluble | 0.24 |
| | 5 Lemon natural, water soluble | 0.10 |
| D | TEA (triethanolamine) | 0.6 |
| E | Hylasome with 47% lactic acid (Step 2) | 5.0 |
| F | 1 HA 1% | 0.19 |
| | 2 Hydrosay 2000 | 0.095 |
| | 3 DxS | 0.0024 |
| | 4 Water | 0.60 |
| | 5 TEA | 0.0033 |
| | 6 Phenonip | 0.0095 |

Step 3: Preparation of Face Mask

To the basic formulation containing the active component Hylasome-lactic acid were added 5 gm of ascorbic acid dispersed in 5 gm of Tween 20, and 5 gm of water. To prepare 100 gm of the face mask, 83.3 gm of this composition and 63 gm of titanium dioxide (TiO$_2$) which had been mixed with 10.4 gm of Tween 20 were mixed. The pH of the face mask was approximately 3.0

Example 6

This example illustrates the preparation of an exfoliating cream with the active ingredient Hylasome swollen with 34% glycolic acid.
Step 1: Preparation of the Active Ingredient (Hylasome-34% Glycolic Acid).

To prepare one (1) kg of this material, 20 gm of mannitol, 26 gm of glycerol, 100 gm of tris-amino (buffer) and 340 gm of glycolic acid were added to 310 ml of RO water (reverse osmosis). These components were stirred together, then 4.0 gm phenonip (preservative) were added to this mixture. To the resulting mixture, 200 gm of Hylasome (HA 1%) were added and the mixture stirred until fully swollen. The equilibrated gel contained HA 0.2% and 34% glycolic acid, with a pH of approximately 3.0
Step 2: Preparation of Exfoliating Cream.

100 gm of exfoliating cream were made by adding 6 gm of the active ingredient complex (Hylasome-34% glycolic acid) to 94 gm of the basic formulation prepared according to Example 5 (Step 2).

Example 7

This example illustrates the preparation of compositions containing Hylasome swollen with ascorbic acid (AA).
Step 1: Preparation of Compositions

| Components | Composition #1 (%, g/100 g) | Composition #2 (%, g/100 g) |
|---|---|---|
| Ascorbic Acid | 9.4 | 9.4 |
| Propylene glycol | 58.0 | 55.3 |
| glycerol | 4.6 | 4.6 |
| Ethyl alcohol | 4.6 | 4.6 |
| Lemon bioflavinoids | 0.46 | 0.46 |
| mannitol | — | 2.7 |
| Carbopol 940 | 0.47 | 0.47 |
| EDTA | 0.10 | 0.10 |
| Phenonip | 0.50 | 0.50 |
| TEA | 1.3 | 1.3 |
| Hylasome (HA 1%) | 10.2 | 10.2 |
| Water (RO) | 10.2 | 10.2 |
| Natural lemon oil, water soluble | 0.17 | 0.17 |

To prepare composition #1, water was added to Hylasome (HA 1%), in equal volumes, and the gel allowed to swell with gentle mixing; the HA concentration in the diluted Hylasome gel was 0.5%. To this gel was added dry powdered ascorbic acid, which dissolved in the network of the hydrated HA gel. Heating was not used to dissolve the AA in the gel. Propylene glycol, glycerol and ethyl alcohol were added and the mixture stirred at room temperature for approximately 1 hour. The Hylasome incorporated with the above ingredients became clear in appearance. To this gel slurry was added Carbopol 940, and after uniform dispersement, the preservatives EDTA and phenonip were added, as well as natural lemon oil (water soluble) and TEA. The gel slurry remained transparent. Composition #2 was prepared following the same procedure, with the exception that mannitol was added to the gel slurry before Carbopol 940 had been dispersed. Composition #2 was cloudy due to the presence of mannitol, which did not fully dissolve in the gel slurry. Mannitol was included in the composition in order to increase the stability of the gel slurry. The pH of both compositions was approximately 4.0.
Step #2: Stability Study of AA in the Gel Slurry (Compositions #1 and #2)

| | Concentration of AA (%) g/100 g | | Reduction of AA, % | |
|---|---|---|---|---|
| Time | Composition #1 | Composition #2 | Composition #1 | Composition #2 |
| 0 | 9.5 | 9.3 | — | — |
| 1 month | 9.6 (no change) | 9.4 (no change) | 0 | 0 |
| 12 months | 8.6 | 8.5 | 10 | 9 |

The stability study was carried out at room temperature (20°-25° C.) and cold temperature (4°-7° C.). Samples were placed into 20 cc transparent glass containers with screw caps. The product occupied two-thirds of the volume of the container. The rest (head-space) was air. Samples which were stored at room temperature were placed under artificial light, and the stability was evaluated by measuring the concentration of AA using a spectrophotometric method, using a Perkin Elmer spectrometer, Model PE Lamda 2. Absorbance values were read at ?max243 (nm). All samples were diluted $10^4$ times using HCl to achieve a pH of approximately 2.0. Each data point in the table represents the average of a minimum of three values from samples of each composition. Absorbance reading were measured two times. Samples which were stored at cold temperatures produced absorbance values which were very close to those from the samples stored at room temperature. Color change was also monitored visually, and were consistent with absorbance values. After 12 months of storage the color of the samples were yellow-amber, this color remained stable for over 20 months.

Composition #3

| Ingredients | % (gm/100 gm) |
|---|---|
| Ascorbic Acid | 10 |
| Glycerol | 43 |
| Mannitol | 5 |
| Hylasome | 22 |
| Propylene Glycol | 20 |

Reduction of AA concentration at different pH after 3 and 6 months of storage (including daylight). The pH was adjusted using TEA.

| Composition Comp. #3 | Original AA. conc, % | Adjusted AA conc, % Original pH | AA concentration, % After 3 mo | After 6 mo | Reduction of AA concentration, % After 3 mo | After 6 mo |
|---|---|---|---|---|---|---|
| | 10.1 | 2.51 pH 3.0 | 9.85 | 9.51 | 2.48 | 5.84 |
| | | 9.67 pH 4.0 | 9.48 | 9.25 | 1.94 | 4.34 |
| | | 8.33 pH 5.0 | 8.16 | 7.92 | 2.04 | 4.92 |
| | | 6.43 | 6.3 | 6.18 | 2.02 | 3.89 |

The data presented in the preceding table shows that there is no correlation between AA stability and pH in compositions in which AA is stabilized by different polyhydroxy compounds.

Example 8

This example illustrates the preparation of a dermatological composition using Hylasome swollen with 50% trichloroacetic acid (TCA) as the active ingredient. To prepare 100 gm of a dermatological peeling composition, 50 gm of TCA were added to 25 gm of water, 2.4 gm of glucose and 2.6 gm of glycerol and the mixture was stirred. To the mixture were added 20 gm of Hylasome (HA 1%) and it was stirred until fully swollen. The pH of the peeling composition was approximately 1.8-2.0.

Example 9

This example illustrates the preparation of the active ingredient Hylasome swollen with a solution in water or saline of low molecular weight HA. To prepare 100 gm of Hylasome-HA gel, 99 gm of 0.1% HA (50,000 MW) were added to 1 gm of Hylasome (HA concentration 1%). Mixing was continued until fully swollen. The total HA content was 0.11% and the swelling ratio was 909. This composition can be used to control the release of low molecular weight HA.

Example 10

This example illustrates the preparation of a composition with the active ingredient Hylasome swollen with high molecular weight HA. To prepare 100 gm of this composition 25 gm of water were added to 25 gm of Hylasome (HA 1%) and mixed until a uniform swollen gel was obtained with a HA concentration of 0.5%. To this gel 50 gm of 0.5% HA solution in water (MW 500,000-6,000,000) were added and mixed until fully swollen. To 90 gm of equilibrated gel 10 gm of Centella Asiatica extract were added and stirred until uniform. This composition is used to treat the skin following other skin treatments such as skin peels and dermabrasion. The total HA concentration was 0.75%, the swelling ratio was 133. This active ingredient may be used as described as a final formulation, or as an ingredient in a formulation to control the release of low molecular weight actives into the skin.

Example 11

This example illustrates the preparation of a composition in which Hylasome (HA 1%) is incorporated with a hydrophobic material that is a sunscreen (Parsol MCX).

Hylasome (HA 1%) was prepared according to Example 1. To Prepare 100 gm of the composition, 4.6 gm of lanoil AWS were added to 4.6 gm of Vitamin E acetate (tocopheryl acetate) and 4.6 gm of Tween 80, and mixed until dissolved. Upon dissolution 41.4 gm of sunscreen Parsol MCX were added and the mixture stirred until a uniform suspension formed. Then 18.4 gm of water were added and mixed, and 18.4 gm of Hyalsome (HA 1%) were added, and mixed until uniform. Then, 7.6 gm of noncrosslinked hyaluronic acid (HA) were added and the mixture stirred. After mixing, 0.4 g of phenonip preservative was added. The composition was homogenized according to the procedure described in Example 2. The concentration of sunscreen in this composition was 41.4%, the concentration of Hylasome (HA 1%) was 18.4%, and the total HA concentration was approximately 0.1% (1 mg/ml). To prepare 1 kg of the final formulation with sunblock properties, 900 g of the basic formulation which was prepared according to Example 2 were added to 100 gm of Hylasome-sunscreen (Parsol MCX) suspension and thoroughly mixed until the consistency was that of a uniform cream. The final formulation had an SPF of 19 (in vitro). The total concentration of sunscreen was 5.04%, Hylasome (HA 1%) was 1.84% and the concentration of HA was approximately 0.12% (1.2 mg/ml). The Hyalsome-Parsol (MCX) composition was able to maintain the topical sunscreen for longer periods of time, and henee the potential to increase the duration of its effect (FIG. 1). There is also the potential to reduce the absorption of sunscreen into the layers of the skin. Sunscreen which has been absorbed into the skin is no longer effective as a sunscreen, and also presents issues of safety due to systemic absorption. The resulting cream was stable and had good hydrating properties, as well as an excellent feel on the skin and a pleasant smell due to the presence of natural oils and botanical extracts.

Example 12

This example describes the preparation of a formulation with the active ingredient capsaicin and Hylasome.

Step 1: Preparation of a Complex of Capsaicin with Hylasome (HA 0.125%).

Hylasome with an HA concentration of 0.125% was prepared according to Example 2 with the exception that 1 part of Hylasome gel was added to 7 parts of water, and phenonip was not added. The resultant gel was loaded with capsaicin (Kalsec, 14% capsicum) at a ratio of gel:capsaicin of 1.33 to 1. The gel was partially swollen with capsaicin.

Step 2: Preparation of the Basic Formulation with Cooling Effect.

This composition was prepared in separate stages as follows: Part A of the mixture was prepared by dispersing Carbopol 940 in water and then stirring until uniform dispersion forms.

| Part | | | Ingredients | Formula % by weight |
|---|---|---|---|---|
| 1 | A | 1 | Carbopol 940 | 0.48 |
|   |   | 2 | water | 73.5 |
|   | B | 3 | Cellosize polymer PCG-10 1% | 7.68 |
|   |   | 4 | Polyox 1% in water | 0.34 |
|   |   | 5 | HA 1% in water | 0.98 |
|   |   | 6 | Ketrol 1% in water | 4.8 |
|   |   | 7 | Phosal 50 | 0.44 |
|   | C | 1 | Robane | 0.14 |
|   |   | 2 | *Macadamia* oil | 0.48 |
|   |   | 3 | Coconut oil | 0.48 |
|   |   | 4 | Olive oil | 0.14 |
|   |   | 5 | Cucumber extract | 0.14 |
|   |   | 6 | Chamomile extract | 0.14 |
|   |   | 7 | *Calendula* extract | 0.48 |
|   |   | 8 | *Aloe Vera* | 0.14 |
|   |   | 9 | Phenonip | 0.75 |
|   |   | 10 | Soy Protein | 0.50 |
|   | D | 1 | Menthol 5% in ethanol | 0.96 |
|   | E | 1 | Triethanolamine | 0.48 |
|   | F | 1 | Lemon Natural Water Soluble | 1.44 |
|   |   | 2 | Rose Natural water soluble | 1.44 |
|   |   | 3 | Dye - FD&C BLUE #1/ FD&C YELLOW #6 9:1, 0.1% in water | 0.07 |
| 2 |   | 1 | Hylasome (HA 0.1%) | 4.0 |

Parts B and C were prepared separately, and the three parts (A, B and C) were heated separately to 50-55° C. Then, Parts A, B and C were combined and cooled to 30-35° C. Then Parts D, E, and F were added and mixed carefully until a uniform gel-based cream formed. Part 2—Hylasome (HA 0.1%) was then added.

Step 3: Preparation of the Final Formulation with Complex: Hylasome-Capsaicin.

To prepare 100 gm of the final formulation, 5 gm of $TiO_2$ were added to 81.7 gm of the basic formulation (Step 2) and stirred well. Then, 13.3 gm of the complex Hylasome (HA 0.125%)-capsaicin were added (Step 1).

Concentration of active ingredients: capsicum: 0.8%; HA: total HA concentration was calculated based on dry polymer, 0.028%. When applied to the skin a slight stinging sensation was observed; this reaction was temporary and disappeared within minutes.

Example 13

This example illustrates the preparation of a formulation in which Hylasome (HA 1%) was incorporated with drugs such as an antibiotic (bacitracin), and a steroid (hydrocortisone or hydrocortisone acetate).

Step 1: Preparation of a Composition in which Hylasome (HA 1%) is Incorporated with Petrolatum.

To prepare 100 gm of this composition, first a mixture of 5 gm of vitamin E acetate with 5 gm of Lanoil AWS and 5 gm of Tween 20 was prepared. 45 gm of petrolatum were added to this composition and mixed carefully. To this mixture were added 20 gm of water, mixed until uniform suspension formed and then 20 gm of Hylasome (HA 1%) were added.

Step 2: Preparation of Hylasome-Drug Composition.

To prepare 25 gm of this composition, 0.45 gm of bacitracin and 1.25 gm of hydrocortisone (and/or hydrocortisone acetate) were added to 23.3 gm of Hylasome-petrolatum and carefully mixed.

Step 3: Preparation of the Final Formulation with Hylasome-Petrolatum-Drugs.

To prepare 100 gm of the final formulation, a dermatological cream, 80 gm of the formulation described in Example 2, Step 3, were added to 20 gm of the composition described in Step 2 of this example. The concentration of the antibiotic in this cream was 0.36%, the concentration of the cortisone was 1%. The concentration of the petrolatum was 8.4%. The final dermatological composition possessed highly hydrating, non-greasy properties due to the presence of Hylasome. This cream was effective in treating dry, cracked skin.

Example 14

This example illustrates the preparation of a composition in which Hylasome (HA 0.1%) which has been very highly homogenized to fine particles into which a drug (povidone iodine) was incorporated. To hylasome (HA 1%) prepared according to Example 2 (100 g) was added 1-12% by wt. of povidone iodine. This composition can be used as an antiseptic, antimicrobial, in the form of liquid drops for the treatment of infections of the ear (otitis externa and otitis media), nose and throat. The composition may also contain seabuckthorn oil (antiseptic) and rose oil for natural fragrance, and a pleasant smell to an otherwise unpleasant smelling composition.

The invention claimed is:

1. A topical composition comprising: hylan B in a non-equilibrium form and antiseptic agent deliverable topically, and wherein hylan B is loaded by swelling with antiseptic agent, alone or in combination with another substance, whereby the antiseptic, alone or in combination with the substance, becomes entrapped within the hylan B gel matrix.

2. A composition according to claim 1, wherein the antiseptic agent is povidone iodine.

3. A composition according to claim 1, wherein said another substance is an inorganic ingredient.

4. A composition according to claim 1, wherein said another substance is selected from the group consisting of α, β, γ, or δ-hydroxy acid, an α-amino acid, a β-amino acid, a γ-amino acid, a δ-amino acid, glycerin, a vitamin, a vitamin derivative, a sugar, an essential oil, a water-soluble oil, a fragrance, a natural polymer, a synthetic polymer, a cross-linked natural polymer, a cross-linked synthetic polymer, a peptide, a protein, a polysaccharide or a nucleic acid.

5. The composition of claim 1, wherein the composition comprises rose oil and/or seabuckthorn oil.

6. The composition of claim 1, wherein hylan B is homogenized.

7. The composition of claim 1, wherein the composition is a gel slurry.

8. The composition of claim 1, wherein the composition is formulated in the form of liquid drops for treatment of infections of the ear, nose or throat.

9. A topical composition comprising: hylan B in a non-equilibrium form and antiseptic agent deliverable topically, and wherein hylan B is loaded by swelling with antiseptic agent, alone or in combination with another substance, thereby the antiseptic, alone or in combination with the substance, becomes entrapped within the hylan B gel matrix and wherein:
   1) the antiseptic agent is povidone iodine; and
   2) the composition is formulated in the form of liquid drops for treatment of infections of the ear, nose or throat.

10. The composition of claim 9, wherein the hylan B gel matrix is homogenized and the composition is a gel slurry.

11. A topical composition, comprising: 1) hylan B in a non-equilibrium form; 2) low molecular weight hyaluronic acid and 3) a therapeutic agent deliverable topically, wherein the therapeutic agent is selected from the group consisting of an anti-inflammatory agent, an antiseptic agent, an anti-infective agent, a mucous membrane agent, a cleansing agent, a preservative, an astringent, an antihistamine, an analgesic, an anesthetic, an acne medication, an antifungal agent, an antipruritic agent, a hormone, a growth factor, a moisturizing agent, a sunscreen, a hyperpigmentation agent, an antioxidant or a nutritional agent.

12. The composition of claim 11, wherein the antiseptic agent is povidone iodine.

* * * * *